United States Patent [19]

Kuboki

[11] Patent Number: 5,135,396
[45] Date of Patent: Aug. 4, 1992

[54] FINE FILLING METHOD AND FINE FILLER FOR DENTAL PURPOSES

[75] Inventor: Yoshinori Kuboki, Sapporo, Japan

[73] Assignee: Kabushiki Kaisha Sangi, Japan

[21] Appl. No.: 545,357

[22] Filed: Jul. 26, 1990

Related U.S. Application Data

[63] Continuation of Ser. No. 407,711, Sep. 14, 1989, abandoned.

[51] Int. Cl.$^5$ .................................................. A61K 5/01
[52] U.S. Cl. .................................. 433/228.1; 526/116; 424/48; 424/49
[58] Field of Search ............................ 433/228.1, 199.1; 424/49, 48; 523/116

[56] References Cited

U.S. PATENT DOCUMENTS

| | | | |
|---|---|---|---|
| 4,556,561 | 12/1985 | Brown et al. | 424/48 X |
| 4,672,032 | 6/1987 | Slavkin et al. | 424/49 X |
| 4,746,686 | 5/1988 | Waller | 523/116 X |

FOREIGN PATENT DOCUMENTS 0219078 4/1987 European Pat. Off. .

OTHER PUBLICATIONS

*Dentistry Journal*, 26(2) 215–223 (1987) in Japanese.
"Dentermination, Reminerlization and Microfilling Restoration Enamel" Biochemical and Biophysical Research Communications 121(2) 592–597 (1984).
"Calcified Tissue International" (1988) 43:389–399.

*Primary Examiner*—V. Millin
*Attorney, Agent, or Firm*—Finnegan, Henderson, Farabow, Garrett & Dunner

[57] ABSTRACT

A fine filling method for dental purposes is characterized in that a fine filler in the form of a powder, a granulate, a suspension or paste, containing finely divided particles of hydroxy-apatite or tetracalcium phosphate, with or without an adjuvant, is rubbed on the surface of a tooth and contacted with saliva. The fine filler for use in this method may contain a calcification-promoting protein.

13 Claims, No Drawings

FINE FILLING METHOD AND FINE FILLER FOR DENTAL PURPOSES

This is a continuation of application Ser. No. 07/407,711, filed Sept. 14, 1989 now abandoned.

BACKGROUND OF THE INVENTION

1. Field of the Invention

The present invention relates to a dental fine filling method for protecting or restoring pits and fissures or minute decalcified surface lesions in enamel by rubbing therein a powder, granules, a solution (suspension) or paste containing hydroxy-apatite or tetracalcium phosphate with or without adjuvants and then optionally covering the site with a polymer or fluoride, and to a dental fine filler used for such filling, which is based on hydroxy-apatite or tetracalcium phosphate which may or may not contain calcination-promoting protein or a coating agent.

2. Description of the Prior Art

When plaque deposits on the surface of enamel, acids produced therein by microorganisms gradually etch the enamel and produce minute lesions therein. (This process is hereinafter referred to as decalcification. It is recognized that decalcified lesions are recalcified and restored by saliva.) One the enamel is decalcified, plaque is soon redeposited on the decalcified lesions, even though it is removed by brushing, so that the enamel is subjected to repeated decalcification due to acids. Thus, decalcification advances through repetitive occurrence of decalcification, removal of the plaque, redeposition of the plaque and decalcification, ending in visually detectable caries. In conventional dental treatment, the hard tissue of a visually detectable carious tooth including its periphery is resected, and various plastics, cements or metals are filled in the resected site as a replacement of the lesion. However, this method requires a high degree of technical skill. In addition, if filling is incomplete, the carious process again advances from the periphery of the filling material. In recent years, a sealant method has been developed in which the pits and fissures that are most susceptible to caries or decalcified lesions caused by the incipient decalcification are occluded with a sealant that is a polyacrylate, polyurethane or other polymer to isolate them from the oral environment, thereby preventing caries from occurring. According to the sealant method, the pits and fissures or decalcified lesions, which may have been treated with acids depending upon the sealant agents used, are occluded therewith to prevent plaque from occurring and acting on the site, thereby preventing caries. In this method, however, insufficient or excessive acid treatment or deposition of saliva on the acid-treated surface may cause a decline in the bonding force of the sealants with respect to pits and fissures or decalcified lesions. The sealants, if occluded in too large an amount, may also break due to mastication and biting. Thus, with the sealant method, there is the possibility that the sealants may dislodge depending upon their quality and the technical skill of the operator, and the effectiveness of the method varies with the clinical skill of the operator. With the sealant method, difficulty is encountered in covering minute decalcified lesions with the sealant agents and in the recalcification of the covered decalcified lesions since they do not come into contact with saliva. In efforts to enhance resistance to caries by the reinforcement or protection of dentin, fluorine ions are applied to the surface of teeth or added to drinking water and foods. However, a special technique is required for the manipulation of fluorine compounds. As a method of depositing an enamel composition on the surface of teeth, Japanese Patent Application Laid-Open (KOKAI) No. 47-1567 proposes to form brassid on the surface of teeth using as the medium a gelatiniform substance prepared in such a manner that its toxicity and final pH do not harm the mouth, and to convert brassid to hydroxy-apatite. However, this method not only requires an extended period of time for the conversion of brassid to hydroxy-apatite, but also requires use of the gelatiniform substance so as to help bond brassid to the surface of teeth.

Application of fluorine exists as a procedure for reinforcing the surface of teeth, and the sealant method or the method disclosed in Japanese Patent Application Laid-Open (KOKAI) No. 47-1567 is available as a procedure for protecting the pits and fissures and restoring decalcified lesions. However, these methods require special clinical skill and involve the difficulties mentioned above.

SUMMARY OF THE INVENTION

As object of the present invention is to provide a dental fine filling method which can easily be carried out in a short period of time with no need for any special clinical skill for safe protection and restoration of pits and fissures and decalcified lesions.

According to the present invention, the foregoing object is attained by providing a fine filling method for dental purposes, characterized in that a powder, a granulate, a solution (suspension) or paste containing hydroxy-apatite with or without an adjuvant is rubbed on the surface of teeth.

Another object of the present invention is to provide a dental fine filler used in the method of the invention.

According to the present invention, the foregoing object is attained by providing a fine filler for dental purposes, characterized in that a calcification-promoting protein is incorporated in hydroxy-apatite or tetracalcium phosphate.

According to the method of the invention, suspensions of finely divided hydroxy-apatite containing radioactive calcium and finely divided brassid were prepared and added to an artificial tooth prepared by sintering hydroxy-apatite for the immersion thereof. The upper face of the artificial tooth was rotatively abraded through a rubber membrane. After elapse of a certain time, the artificial tooth was removed and, soon thereafter, a large amount of distilled water was added dropwise thereto for washing, followed by the addition of a PSC cocktail. Radioactivity of the artificial tooth was measured with a liquid scintillation counter, whereby the amounts of hydroxy-apatite and brassid bonded to the artificial tooth were determined. As a result, it was found that the bonded amounts depended upon the pH of the suspensions, but the amount of hydroxy-apatite bonded was much larger than the amount of brassid bonded in any pH range. It was also confirmed by nominal experimentation that tetracalcium phosphate [$Ca_4(PO_4)_2O$] obtained by sintering an equimolar mixture of tricalcium phosphate and calcium oxide at 1500° C. bonded easily to a tooth, as was the case with hydroxy-apatite, and the tetracalcium phosphate bonded changed to hydroxy-apatite immediately upon contact with saliva to promote the recalcification of the tooth. The fact that these substances promote the recalcification of teeth and protect the teeth from decay was supported by the following experimentation. An extracted 3rd molar subjected to artificial caries was immersed under agitation in a hydroxy-apatite or tetracalcium phosphate paste at 37° C. for 5 hours, and the surface enamel layer of the tooth was thereafter observed under a polarization microscope. As a result, decalcified lesions were found over a wide range of the control group, whereas the hydroxy-apatite or tetracalcium phosphate-treated group was recalcified on the surface layer, with the decalcified lesions being thinner than those of the control group. These indicate that hydroxy-apatite or tetracalcium phosphate is efficiently bonded to the surfaces of teeth to cover or cure the decalcified lesions and promotes the recalcification of enamel by contact with saliva. Thus, the present invention provides a method for the protection of pits and fissures or for the restoration of decalcified lesions by making use of the properties of hydroxy-apatite or tetracalcium phosphate bonding selectively to the surface decalcified lesions of teeth. The invention also provides a fine filler used in the method.

It is desired that the hydroxy-apatite or tetracalcium phosphate to be used be as finely divided as possible. In general, they are finely divided to about 0.02 to 10 microns for use. The finely divided hydroxy-apatite or tetracalcium phosphate is formulated to about a 5 to 95% solution (suspension) or paste with or without water or a coating agent. These materials are rubbed on a tooth, from which the plaque has been removed, with a fingertip, brush, stick, cloth or the like for at least 1 min, preferably 3 min. In the course of this operation, the hydroxy-apatite or tetracalcium phosphate is further finely divided and bonded to the pits and fissures or minute decalcified lesions of the enamel. Since the hydroxy-apatite or tetracalcium phosphate is the highest nutritive calcium substance, the patient may swallow extra calcium salts remaining in the mouth. Preferably, washing of the mouth with water should be carried out lightly and limited to about one time. The recalcification of the hydroxy-apatite or tetracalcium phosphate bonded to the tooth surface is promoted due to the presence of saliva.

It is preferred to use powders, granules, solutions (suspensions) or pastes of hydroxy-apatite or tetracalcium phosphate which are prepared by mixing with a suitable amount of an adjuvant selected from a phosphate such as tricalcium phosphate and monohydrogen calcium phosphate; a fluoride such as sodium fluoride, sodium monofluorophosphate, apatite fluoride and stannous fluoride; calcification-promoting protein such as phosvitin, casein and histidine-rich protein (these proteins were found to act as the catalysts and accelerators for the calcification of hydroxy-apatite); or a mixture thereof, since the adjuvant promotes the recalcification of the decalcified lesions and reinforces the covered layer. The amounts of these adjuvants to be added may be selected arbitrarily depending upon their types. In general, however, the phosphate should be used in amounts of about 1 to 60%, the fluoride in an amount of 1000 ppm at most and the calcification-promoting protein in an amount of about 1% at most, with respect to the hydroxy-apatite and/or tetracalcium phosphate. The coating agent used for the paste may be vinyl acetate, glue, polyacrylic acid, gum arabic or the like.

Thus, the hydroxy-apatite or tetracalcium phosphate is bonded to the surface of teeth merely by rubbing thereon the hydroxy-apatite or tetracalcium phosphate-containing paste, and is recalcified by saliva. The presence of the adjuvants serves to enhance such recalcification and the strength of teeth. The method according to the present invention can easily be carried out without recourse to acid treatments, moisture-proofing and polymerization treatments applied in the conventional sealant method, and without any special clinical skill. Further, the hydroxy-apatite, tetracalcium phosphate, adjuvants and coating agents have no adverse influence upon the living body. Still further, the hydroxy-apatite is a component the same as that found in teeth, while the tetracalcium phosphate is easily converted to hydroxy-apatite by saliva. Thus, since these substances do not constitute foreign matter with respect to teeth, unlike the prior art sealant agents, and since they bond firmly to the pits and fissures and decalcified lesions with no risk of being dislodged, completely restored teeth are produced. In addition, plasticizers, solvents, diluents and so on may be added to the paste comprising hydroxy-apatite or tetracalcium phosphate and the calcification-promoting protein and coating agent in such a manner that the resulting system has a viscosity suitable for covering the surface of teeth and providing a film of uniform thickness. The application of such a system to the surface of teeth is advantageous in that the surface of teeth can be reinforced an improved in appearance.

It is also possible to reinforce teeth by rubbing the hydroxy-apatite or tetracalcium phosphate-containing powders, granules, solutions (suspensions) or pastes on the surfaces thereof, followed by the application of fluoride. It is particularly preferable to rub on the paste containing hydroxy-apatite or tetracalcium phosphate and the calcification-promoting protein and, thereafter, apply fluoride thereon in the conventional manner. It is also possible to rub the paste on the surface of teeth and thereafter cover and protect the site with a polymer. The polymers used to this end may be selected from polymers so far used as the sealants, such as Epoxylight 9070, Nuva-Seal, Epoxylight 9075, Enamelight, Delton, White Sealant, P & F Sealant, Fissureseal, Teethmata S, Prisma Shield, Helioseal, or polymers used with sustained release preparations for pharmaceuticals such as shellac, polyvinyl acetate, polyvinyl butyral, ethyl cellulose, cellulose acetate phthalate, polyvinyl alcohol phthalate, styreneacrylic acid copolymers, methyl acrylate-methacrylic acid copolymers, copolymers of vinyl pyridine or alkyl pyridine with other vinyl monomers, cellulose acetate diethylaminoacetate, polyvinyl acetate diethylaminoacetate, polyvinyl aminoacetal, polyvinyl alcohol derivatives, amino cellulose derivatives, dimethylaminoethyl methacrylate-methyl methacrylate copolymers and copolymers of vinyl pyridine or alkylvinyl pyridine with acrylic acid. These polymers may be applied to the site in the conventional manner. The hydroxy-apatite or tetracalcium phosphate and adjuvants rubbed in place by this coating are retained on the surface of the teeth over an extended period of time without being dislodged, and are efficiently recalcified. The hydroxy-apatite or tetracalcium phosphate and calcification-promoting protein-containing paste may be added with, e, g., pharmaceutically active components such as an abrasive selected from calcium carbonate, calcium hydrogen phosphate, aluminum hydroxide, silicic anhydride and other abrasives; a humectant such as glycerin, sorbitol and propylene glycol; a foaming agent such as sodium lauryl sulfate and soap powders; a binder such as carboxymethylcellulose and carrageenan; a perfume; a sweetener, a preservative; and a halitosis remover and tooth detinter. To use this system in a manner similar to a dentifrice provides a usable procedure which makes it possible to remove plaque simultaneously with rubbing of the hydroxy-apatite or tetracalcium phosphate and calcification-promoting protein on to the surface of teeth.

Thus, there is provided a method for remedying the decalcification that is the incipient state of caries, which method makes use of the properties of the adjuvant-containing or free hydroxy-apatite, which is the same component as tooth, or tetracalcium phosphate bonding selectively and firmly to the pits and fissures or decalcified lesions, and in which the hydroxy-apatite or tetracalcium phosphate is rubbed on the surface of teeth with or without adjuvants to protect the surface of the teeth or cover the decalcified lesions for the purpose of taking advantage of spontaneous healing power obtained through recalcification by saliva. There is also provided a filler used in the above-described method. The tooth-reinforcing and caries-preventing method and filler, which were not available until now, do not require any special technical skill and have considerable technical advantages over the conventional fluoride coating and sealant methods.

Other features and advantages of the present invention will be apparent from the following description.

DESCRIPTION OF THE PREFERRED EMBODIMENT

The present invention will now be described in detail with reference to a number of examples.

EXAMPLE 1

Fifty (50) g of hydroxy-apatite finely divided to 10 microns or less to which 50 ml of water was added was treated in a chaser mill to obtain a paste. Shortly after the teeth were brushed with a dentifrcce followed by rinsing, the paste was carefully rubbed on the surface of the teeth with a fingertip for 3 min. Afterwards, excess paste was removed from within the mouth by light rinsing This procedure was carried out whenever teeth were brushed.

EXAMPLE 2

Fifty (50) g of hydroxy-apatite finely divided to 10 microns or less to which 50 ml of an aqueous solution containing 500 ppm of sodium fluoride was added was treated in a chaser mill to obtain a paste. At the completion of ordinary brushing, teeth were brushed for 3 min with a toothbrush to which paste was applied. This was followed by light rinsing. This brushing was always carried out after ordinary brushing.

EXAMPLE 3

Fifty (50) g of hydroxy-apatite finely divided to 10 microns or less to which 50 ml of water containing 0.01 mg of casein was added was treated in a chaser mill to obtain a paste. At the completion of ordinary brushing, the paste was carefully rubbed on the surface of the teeth with a fingertip for 3 min. This procedure was carried out whenever teeth were brushed.

EXAMPLE 4

In a manner similar to that described in Example 3, the paste was rubbed on the surface of teeth and excess paste within the mouth was then washed away by rinsing. Following drying, a Nuva-Seal liquid was thinly applied to the surface of the teeth and was hardened by an ultraviolet lamp for sealing purposes.

EXAMPLE 5

In a manner similar to that described in Example 3, the paste was rubbed on the surface of teeth and excess paste within the mouth was then washed away by rinsing. Diamine silver fluoride was applied in the conventional manner.

EXAMPLE 6

Four (4) g of hydroxy-apatite finely divided to 10 microns or less and 0.04 mg of casein were added to and mixed sufficiently with 100 ml of vinyl acetate to prepare a homo-geneous dispersion. After ordinary brushing, the teeth were dried with warm air and then uniformly coated with the dispersion by means of a brush. Drying gave a glossy, white and fine coating on the surface of the teeth.

EXAMPLE 7

Fifty (50) g of tetracalcium phosphate finely divided to 10 microns or less to which 50 ml of water was added was treated in a chaser mill to obtain a paste. Shortly after teeth were brushed with a dentifrice followed by thorough rinsing, the paste was carefully rubbed on the surface of the teeth with a fingertip for 3 min. Afterwards, excess paste was removed from within the mouth by light rinsing. This procedure was carried out whenever teeth were brushed.

EXAMPLE 8

Fifty (50) g of tetracalcium phosphate finely divided to 10 microns or less to which 50 ml of an aqueous solution containing 500 ppm of sodium fluoride was added was treated in a chaser mill to obtain a paste. At the completion of ordinary brushing, teeth were brushed for 3 min with a toothbrush to which the paste was applied. This was followed by light rinsing. This brushing was always carried out after ordinary brushing.

EXAMPLE 9

Fifty (50) g of tetracalcium phosphate finely divided to 10 microns or less to which 50 ml of water containing 0.01 mg of casein was added was treated in a chaser mill to obtain a paste. At the completion of ordinary brushing, the paste was carefully rubbed on the surface of the teeth with a fingertip for 3 min. This procedure was carried out whenever teeth were brushed.

EXAMPLE 10

In a manner similar to that described in Example 3, the paste was rubbed on the surface of teeth and excess paste within the mouth was then washed away by rinsing. Following drying, a Nuva-Seal liquid was thinly applied to the surface of the teeth and was hardened by an ultraviolet lamp for sealing purposes.

EXAMPLE 11

Four (4) g of tetracalcium phosphate finely divided to 10 microns of less and 0.04 mg of casein were added to and mixed sufficiently with 100 ml of vinyl acetate to prepare a homogeneous dispersion. After ordinary brushing, the teeth were dried with warm air and then uniformly coated with the dispersion by means of a brush. Drying gave a glossy, white and fine coating on the surface of the teeth.

REFERENCE EXAMPLE

In order to measure the amount of hydroxy-apatite bonded to the surface of a tooth, the following in vitro tests were conducted:

(A) Synthesis of hydroxy-apatite and brassid

One hundred (100) ml of a 0.1 M $CaCl_2$ solution (containing $^{45}CaCl_2$ manufactured by Aeroham) was slowly added dropwise, under agitation, to 100 to 200 ml of 0.1M $Na_2HPO_4$ solutions to synthesize hydroxy-apatite in the conventional manner. On the other hand, a 0.1M $^{45}CaCl_2$ solution was similarly added dropwise to 100 to 200 ml of 0.01 $NaH_2PO_4$ solutions to prepare brassid. After preparation, the hydroxy-apatite and brassid were preserved in the corresponding 0.1 M $Na_2HPO_4$ and 0.1 M $NaH_2PO_4$ solutions. For use, they were resuspended in 0.01 M phosphoric acid buffers of the corresponding pH.

(B) Preparation of artificial tooth

The hydroxy-apatite was molded into a disc which was 1 cm in diameter and 3 mm in thickness, and the disc was sintered to form a hydroxy-apatite tablet, the surface of which was evenly abraded with No. 600 sand paper. Afterwards, the tablet was brushed to carefully remove powders, while distilled water flowed thereover, thereby making an artificial tooth.

(C) An acryl tank which was 12 cm in length, 4 cm in width and 10 mm in depth was provided in its bottom with five blind holes for the fixation of hydroxy-apatite tablets, each of which was 1 cm in diameter and 2 mm in depth. Five hydroxy-apatite tables were fixed in the blind holes and 5 ml of a hydroxy-apatite or brassid suspension was added to immerse the tablets. The upper surface of the tablets was abraded at 1 rpm. Upon elapse of a certain time, the tablets were removed and, soon thereafter, washed by dropwise addition of a large amount of distilled water. Two (2) ml of a PSC cocktail was added to the tablets to measure the radioactivity of the tablets with a liquid scintillation counter.

(D) Results

As the results of tests performed at pH 9.0 and 5.0 that were the stable pH of hydroxy-apatite and brassid, respectively, the amount of hydroxy-apatite bonded to the tablets was 5 micrograms after 5 min. Thereafter, this increased gradually and reached 164 micrograms after 40 min, as calculated from $5.4 \times 10^5$ CPM/mg and $8.9 \times 10^5$ CPM/mg that where the specific radioactivities of the hydroxy-apatite and brassid used, respectively. This bonded amount was much larger than that of brassid by a factor of 20 after 5 min and 109 after 40 min.

From the results of tests performed at pH 5.5, 6.8, 7.4 and 8.5, where rubbing was carried out at the same pH, it was also found that the bonding force of hydroxy-apatite to the tablets was markedly increased. These results are tabulated below.

| pH Condition | | A/B After 10 min | A/B After 60 min |
|---|---|---|---|
| A: pH 9, | B: pH 5 | 32.8 | 201.7 |
| A, B | pH 8.5 | 2.0 | 5.4 |
| A, B | pH 7.4 | 6.6 | 5.4 |
| A, B | pH 6.8 | 2.3 | 6.4 |
| A, B | pH 5.5 | 11.2 | 8.4 |

A: hydroxy-apatite; B: brassid
Figures represent the amounts in weight ratio of hydroxy-apatite and tetracalcium phosphate bonded to the tablets.

These results reveal that hydroxy-apatite is selectively bonded to the surface of teeth.

Thus, according to the method of the present invention, a fine filler containing hydroxy-apatite that is a biomaterial firmly bonding to the pits and fissures or minute decalcified lesions in the surfaces of teeth or tetracalcium phosphate with or without adjuvants is rubbed on the surface of teeth, optionally followed by covering the thus rubbed site with a polymer, to cover the pits and fissures or decalcified lesions with the fine filler, so that spontaneous healing power is augmented under the action of saliva or the adjuvants for the restoration of the decalcified lesions. This method exhibits excellent effects merely by rubbing the fine filler on the surface of teeth. Since hydroxy-apatite or tetracalcium phosphate is the most ideal calcium substance, it is harmless if swallowed and the filler can be used without fear of harmful effects. No special clinical skill is required to carry out this method. Accordingly, the method of the invention is advantageous in that it can easily be carried out by the patient himself.

The present method in which caries is suppressed in its incipient stage by making use of, and augmenting, spontaneous healing power obtained through recalcification by saliva is the most effective means for preventing caries that is not found in the prior art. The present invention is also applicable to the treatment of paresthesia and pyrrhoea alveolaris.

What is claimed is:

1. A dental fine filling method for protecting or restoring pits, fissures or minute decalcified surface lesions in the enamel of a tooth which method comprises rubbing on the surface of the tooth a fine filler containing finely divided particles of hydroxy-apatite or tetracalcium phosphate and contacting said fine filler with saliva, whereby said hydroxy-apatite or tetracalcium phosphate is bonded to the tooth and recalcification of the tooth is promoted due to the presence of saliva.

2. The method of claim 1, wherein said fine filler further contains a fluoride or calcium phosphate adjuvant effective to promote said recalcification.

3. The method of claim 1, wherein said fine filler further contains a calcification promoting protein selected from the group consisting of phosvitin, casein and histidine-rich protein.

4. The method of claim 1, wherein said hydroxy-apatite or tetracalcium phosphate has a particle size within the range of 0.02 to 10 microns.

5. A fine filler for dental purposes comprising finely divided particles of hydroxy-apatite or tetracalcium phosphate and a calcification promoting protein selected from the group consisting of phosvitin, casin and histidine-rich protein.

6. The fine filler of claim 5, wherein said hydroxy-apatite tetracalcium phosphate has a particle size within the range of from about 0.02 to 10 microns.

7. The fine filler of claim 5, wherein said protein is present in an amount not more than about 1% by weight with respect to said hydroxy-apatite or tetracalcium phosphate.

8. The fine filler of claim 5, further comprising a fluoride or calcium phosphate adjuvant effective to promote recalcification.

9. The fine filler of claim 8, wherein said adjuvant is a fluoride present in an amount of not more than 1000 ppm with respect to said hydroxy-apatite or tetracalcium phosphate.

10. The fine filler of claim 8, wherein said adjuvant is calcium phosphate in an amount in the range of from about 10 to 60% by weight with respect to said hydroxy-apatite or tetracalcium phosphate.

11. The fine filler of claim 5, further comprising a coating agent.

12. The fine filler of claim 5, wherein said fine filler is in the form of a powder, granules, a suspension or a paste.

13. A dental fine filling method for protecting or restoring pits, fissures or minute decalcified surface lesions in the enamel of a tooth which method comprises rubbing on the surface of the tooth a fine filler containing finely divided particles of hydroxy-apatite or tetracalcium phosphate, contacting said fine filler with saliva, whereby said hydroxy-apatite or tetracalcium phosphate is bonded to the tooth and recalcification of the tooth is promoted due to the presence of saliva, and covering the site of the tooth on which said fine filler has been rubbed with a polymer or fluoride.

* * * * *

UNITED STATES PATENT AND TRADEMARK OFFICE
CERTIFICATE OF CORRECTION

PATENT NO. : 5,135,396
DATED : August 4, 1992
INVENTOR(S) : Yoshinori Kuboki

It is certified that error appears in the above-identified patent and that said Letters Patent is hereby corrected as shown below:

Claim 5, column 8, line 53, "casin" should read --casein--.

Signed and Sealed this

Twenty-fourth Day of August, 1993

Attest:

BRUCE LEHMAN

Attesting Officer

Commissioner of Patents and Trademarks